United States Patent
Moore

(10) Patent No.: US 10,786,433 B2
(45) Date of Patent: Sep. 29, 2020

(54) BUFFERING AGENT CARTRIDGE

(71) Applicant: William J Moore, Redding, CA (US)

(72) Inventor: William J Moore, Redding, CA (US)

( * ) Notice: Subject to any disclaimer, the term of this patent is extended or adjusted under 35 U.S.C. 154(b) by 186 days.

(21) Appl. No.: 15/703,952

(22) Filed: Sep. 13, 2017

(65) Prior Publication Data

US 2019/0076332 A1 Mar. 14, 2019

(51) Int. Cl.
| | |
|---|---|
| *A61J 1/20* | (2006.01) |
| *A61J 1/06* | (2006.01) |
| *A61M 5/28* | (2006.01) |
| *A61M 5/31* | (2006.01) |
| *A61M 19/00* | (2006.01) |
| *A61M 5/315* | (2006.01) |
| *A61M 5/19* | (2006.01) |

(52) U.S. Cl.
CPC ............. *A61J 1/2096* (2013.01); *A61J 1/062* (2013.01); *A61J 1/201* (2015.05); *A61J 1/2072* (2015.05); *A61J 1/2093* (2013.01); *A61M 5/19* (2013.01); *A61M 5/284* (2013.01); *A61M 5/286* (2013.01); *A61M 5/3137* (2013.01); *A61M 5/31511* (2013.01); *A61J 1/2027* (2015.05); *A61M 19/00* (2013.01); *A61M 2005/3132* (2013.01)

(58) Field of Classification Search
CPC .......... A61J 1/062; A61J 1/201; A61J 1/2027; A61J 1/2072; A61J 1/2093; A61J 1/2096; A61M 19/00; A61M 2005/3132; A61M 5/19; A61M 5/284; A61M 5/285; A61M 5/286; A61M 5/3137; A61M 5/31511
See application file for complete search history.

(56) References Cited

U.S. PATENT DOCUMENTS

| | | | | |
|---|---|---|---|---|
| 3,718,139 | A * | 2/1973 | Hanford | A61M 5/31596 604/87 |
| 3,779,371 | A * | 12/1973 | Rovinski | A61J 1/2089 206/221 |
| 3,838,689 | A * | 10/1974 | Cohen | A61M 5/31596 604/90 |
| 4,331,146 | A * | 5/1982 | Brignola | A61M 5/286 604/200 |
| 4,693,706 | A * | 9/1987 | Ennis, III | A61M 5/31596 604/87 |
| 6,740,062 | B2 * | 5/2004 | Hjertman | A61M 5/30 604/131 |

(Continued)

FOREIGN PATENT DOCUMENTS

DE 3618318 * 12/1987 ............. A61M 5/28

*Primary Examiner* — Quynh-Nhu H. Vu
(74) *Attorney, Agent, or Firm* — James A. Italia; Italia IP

(57) ABSTRACT

A cartridge for dispensing a pre-measured buffering agent together with a medical fluid such as dental anesthetic. The cartridge includes a sharp piercing element at one end, a frangible barrier proximate the piercing element, and a traveling closure. The buffering solution is in a chamber between the barrier and the closure. When loaded into a syringe and subjected to operating pressures, the barrier is pierced, enabling the buffering solution to mix with the medical fluid. Continued pressure propels a desired, controlled mixture into a tissue of a patient. A dye may be included for visual confirmation of mixing. The invention may be regarded as the cartridge, a syringe having the cartridge, or a kit, with or without a syringe, or cartridges having closures of different types.

5 Claims, 3 Drawing Sheets

(56) References Cited

U.S. PATENT DOCUMENTS

| | | | | |
|---|---|---|---|---|
| 7,435,237 B2 * | 10/2008 | Tan | ............. | A61M 5/19 604/187 |
| 2004/0122359 A1 * | 6/2004 | Wenz | ............. | A61M 5/31511 604/82 |
| 2008/0203112 A1 * | 8/2008 | Peuker | ............. | A61M 5/19 222/137 |
| 2010/0203171 A1 * | 8/2010 | Wright | ............. | A61K 9/124 424/700 |
| 2015/0141913 A1 * | 5/2015 | Bartlett, II | ............. | A61J 1/2093 604/90 |
| 2016/0101881 A1 * | 4/2016 | Wright | ............. | A61K 47/02 128/202.16 |
| 2018/0344933 A1 * | 12/2018 | Dittrich | ............. | A61M 5/286 |

\* cited by examiner

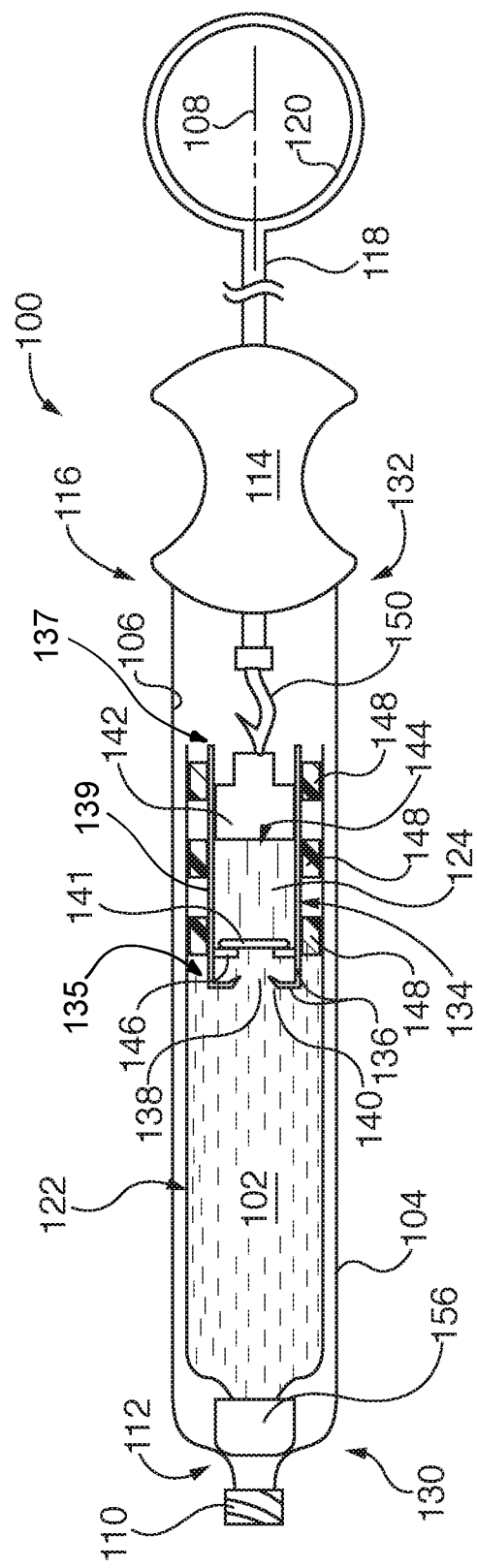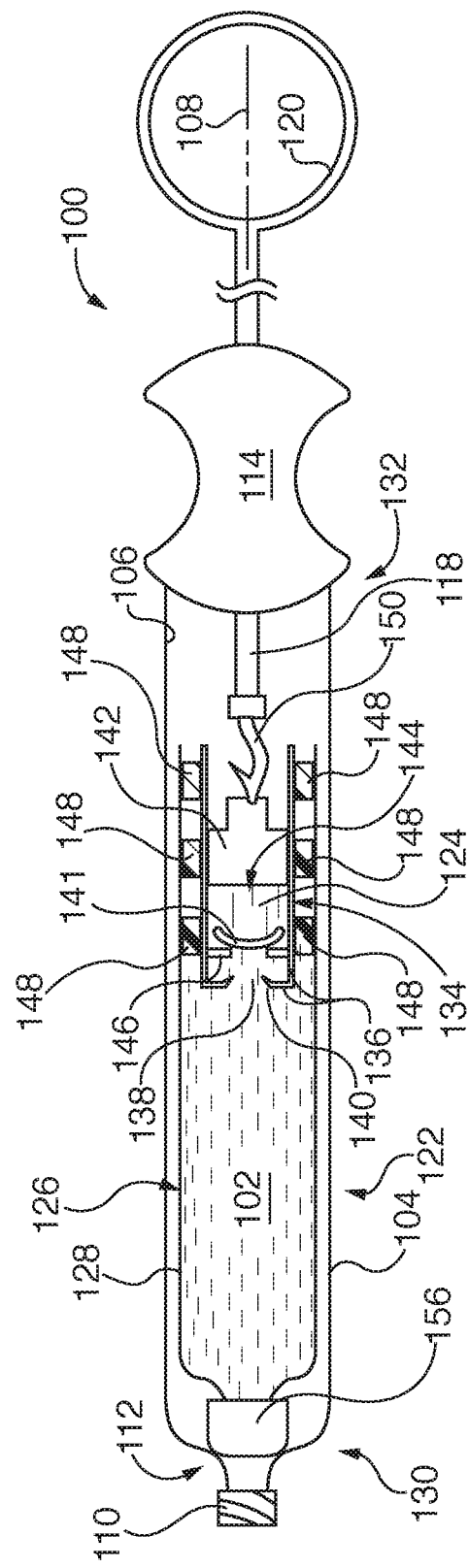

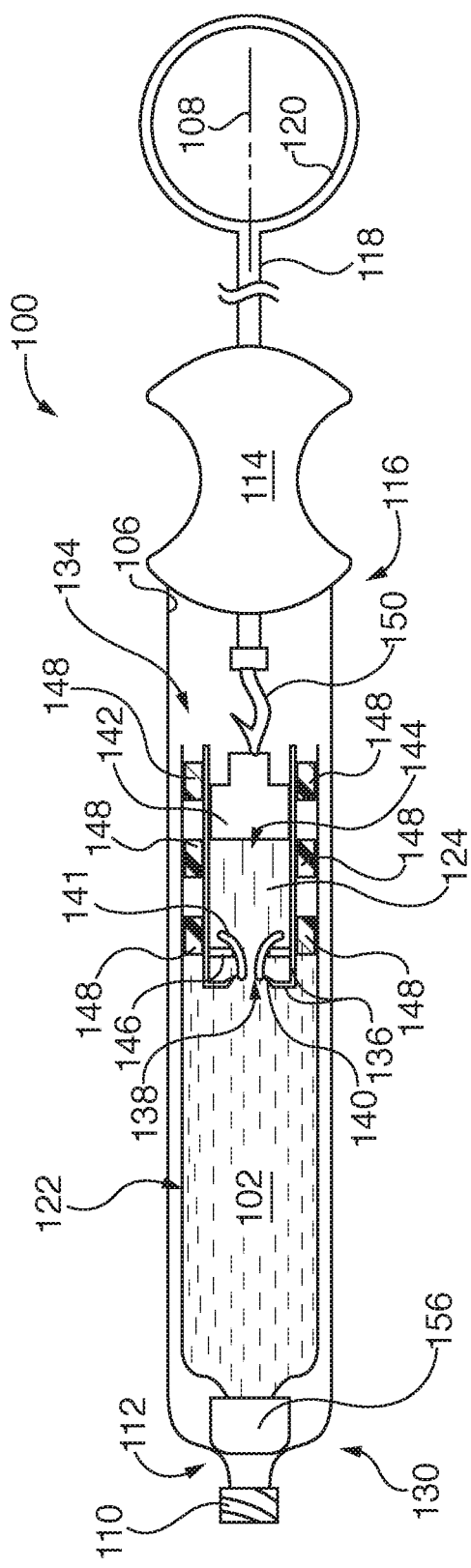
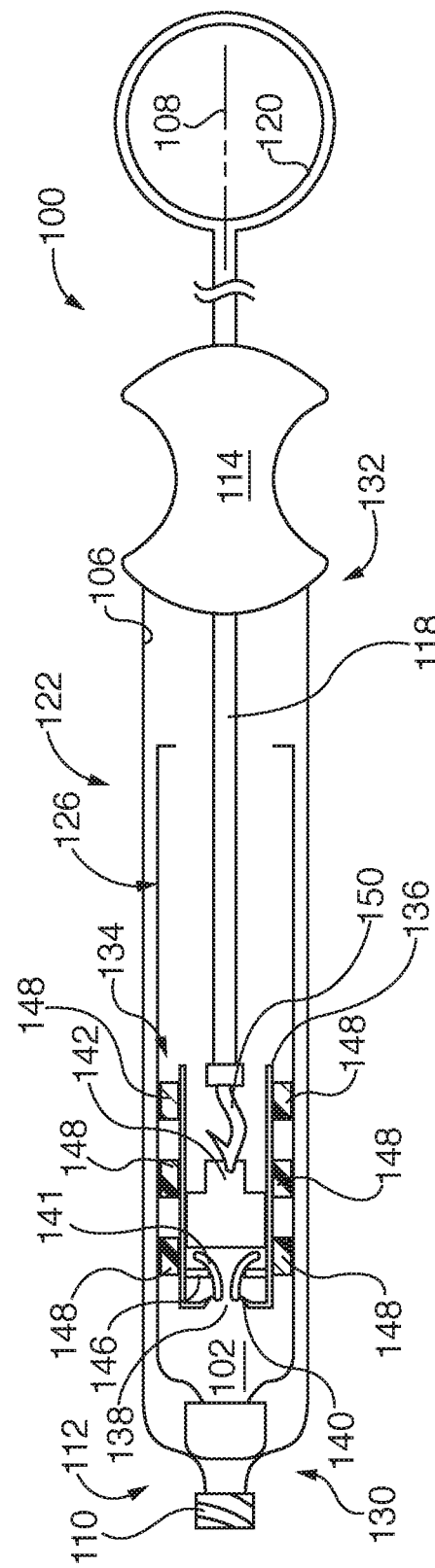
FIG. 3
FIG. 4

BUFFERING AGENT CARTRIDGE

FIELD OF THE DISCLOSURE

The present disclosure relates to dental anesthetic carpules, and more particularly, to adapting a dental anesthetic carpule to include a pre-measured buffering agent cartridge.

BACKGROUND

Dental anesthetic solutions must typically be buffered prior to administration. Buffering is conventionally performed by mixing a buffering agent with anesthetic fluid. Dental personnel typically draw anesthetic solution and separately, a fluid buffering agent into a syringe and mix the two prior to administration. In dental situations, buffered anesthetic has a limited useful life, on the order of thirty seconds, during which it must be used.

This procedure introduces a number of variables into administration of dental solutions, and consequently threatening appropriately metered mixtures.

SUMMARY

The disclosed concepts address the above stated situation by providing apparatus enabling a pre-metered amount of buffering solution to be added automatically to a dental solution. Also, mixing of the buffering solution and injection of the dental solution are performed in one operation. These results are achieved by providing a cartridge containing the pre-metered amount of buffering solution as part of a carpule for an injection syringe. The syringe may be utilized in conventional fashion, with a plunger being depressed by hand. Using the novel apparatus, the plunger propels a slideable closure that leads to the rupturing of a frangible barrier to release the buffering solution. The buffering solution is then propelled into the anesthetic solution. Continued pressure on the plunger then injects the mixed dental solution and buffering solution into tissue of a patient. Time required to properly prepare and administer dental anesthetic is minimized. A desired amount of buffering solution may be selected from a prepared cartridge, so that medical personnel need not prepare a required quantity of buffering solution under time pressure.

Use of dye in the buffering solution allows the medical personnel to assure that proper mixing of buffering agent has occurred, and also, to assure that a limited time window during which newly mixed solution must be used has not expired.

It is an object to provide improved elements and arrangements thereof by apparatus for the purposes described which is inexpensive, dependable, and fully effective in accomplishing its intended purposes.

These and other objects will become readily apparent upon further review of the following specification and drawings.

BRIEF DESCRIPTION OF THE DRAWINGS

Various objects, features, and attendant advantages of the disclosed concepts will become more fully appreciated as the same becomes better understood when considered in conjunction with the accompanying drawings, in which like reference characters designate the same or similar parts throughout the several views, and wherein:

FIG. 1 is a diagrammatic side cross sectional view of a syringe for dispensing buffering solution, according to at least one aspect of the disclosure;

FIG. 2 is similar to FIG. 1, but shows internal components of the syringe in an early stage of injection, according to at least one aspect of the disclosure;

FIG. 3 is similar to FIG. 2, but shows a further stage of injection, according to at least one aspect of the disclosure;

FIG. 4 is similar to FIG. 3, but shows a final stage of injection, according to at least one aspect of the disclosure;

DETAILED DESCRIPTION

Figure 6:
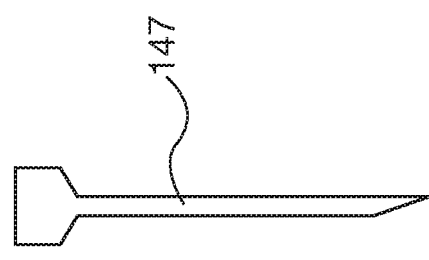
FIG. 6 is a side view of a syringe according to at least one further aspect of the disclosure.

Referring first to FIG. 1, according to at least one aspect of the disclosure, there is shown a syringe 100 for storing then dispensing a first solution (e.g., buffering solution 124) into a second solution (e.g., medical fluid 102, FIG. 2) prior to injection of the mixesolution (medical fluid 102 and buffering solution 124). Syringe 100 may comprise a barrel 104 for containing and dispensing the second solution, barrel 104 including an inner surface 106 and a longitudinal axis 108 within barrel 104, an injection element 110 at one end 112 of barrel 104, a finger grip 114 at an opposed end 116 of barrel 104, a plunger 118 slidably disposed within barrel 104, and a thumb engaging surface 120 coupled to the plunger 118 outside barrel 104. Syringe 100 may also comprise a carpule 122 (shown loaded into barrel 104 in FIG. 1, and seen drawn to enlarged scale in FIG. 2) for dispensing a buffering solution 124 (FIG. 2) into medical fluid 102. Carpule 122 may comprise a body 126 comprising a lateral wall 128 having an injection end 130 and a pressure end 132, and a central axis 108 (identical to longitudinal axis 108 in the embodiment of FIG. 1, wherein barrel 104 and carpule 122 are coaxial) extending between injection end 130 and pressure end 132.

A solution cartridge 134 for storing and then dispensing first solution 124 is slidable within carpule body 126. Referring to FIG. 1, a solution cartridge 134 includes a first end 135, second end 137, and an exterior surface 139 is shown and may further comprise a receptacle 136 including a passageway 138 closed by a frangible barrier 141 configured to close passageway 138, and one or more pointed projections 140 facing a frangible barrier 141. When frangible barrier 141 is urged towards injection end 130, pointed projections 140 assist in rupturing frangible barrier 141. A slidable closure 142 within cartridge 134 causes a first solution chamber 144 to exist within cartridge 134 between frangible barrier 141 and slidable closure 142. Frangible barrier 141 of cartridge 134.causes a second solution chamber 145 to exist within barrel 104 between injection element 110 of barrel 104 and the frangible barrier 141. Slidable closure 142 is located proximate pressure end 132 of carpule 122, thereby causing a first solution chamber 144 to exist within cartridge 134 between frangible barrier 141 and slidable closure 142. Slidable closure 142 is configured to fit slidably and closely within cartridge 134, and to seal first solution chamber 144 against fluid leakage when slidable closure 142 slides along cartridge 134.

First solution 124 may be a buffering solution contained within first solution chamber 144. Second solution 102 may be an anesthetic solution contained within second solution chamber 145.

Injection element 110 may be any structure associated with an injection needle. As depicted in FIGS. 1-4, injection element 110 comprises a threaded hub for threadably receiving a needle 147 (see FIG. 6). It would be possible to fabricate needle 147 integrally with barrel 104, in which case injection element 110 would be the needle.

Thumb engaging surface 120 may comprise a thumb ring, for example, but need not be limited to that. Thumb engaging surface could comprise a dished pad, for example.

Pointed projection 140 may comprise a continuous wall presenting a continuous sharp edge to frangible barrier 141, presenting a series of teeth to frangible barrier 141, or may comprise any arrangement piercing frangible barrier 141 when the latter is pressed against pointed projection 140. Frangible barrier 141 may comprise a thin sheet of a polymeric material, for example. It would be possible to have frangible barrier 141 rupture responsive to pressure rather than being pierced by pointed projection 140. Regardless of the specific cause of rupture, frangible barrier is configured to rupture when urged toward injection end 130.

Slidable closure 142 may be fabricated from a natural or synthetic rubber, and slides within cartridge 134 independently of carpule 122 moving within barrel 104, as will be described hereinafter.

Cartridge 134 may further comprise a stop 146 within chamber 144 adjacent to injection end 130. The stop 146 is located between the slidable closure 142 and frangible barrier 141, and includes passageway 138 extending entirely through stop 146. Stop 146 may comprise an inward projection fixed to cartridge wall 136. As will be explained hereinafter, stop 146 arrests movement of slidable closure 142, and transmits force to cartridge 134.

Slidable closure 142 is arranged to slide in a direction parallel to central axis 108. Manual force propelling slidable closure 142 within cartridge 134 is transmitted to cartridge 134 at a predetermined point when slidable closure 142 is arrested by stop 146. At that point, manual force will then move cartridge 134 within carpule 122. Of course, there may not be direct contact between slidable closure 142 and stop 146, as frangible barrier 141 may intervene and transmit forces from slidable closure 142 to stop 146.

Cartridge 134, and therefore carpule 122, may further comprise a dye of a predetermined color in first solution 124.

Cartridge 134 may further comprise an external seal surrounding and contacting cartridge 134. The external seal may comprise for example a plurality of flexible polymeric rings 148 distributed along cartridge 134. The external seal both prevents escape of second solution 102 towards the rear of barrel 104 (i.e., away from needle 147), and also guides cartridge 134 within a carpule 122 as cartridge 134 slides under pressure from plunger 118.

It should be noted that frictional characteristics of slidable closure 142 and the external seal of cartridge 134 are selected such that there is greater friction between the external seal and lateral wall 128 than between slidable closure 142 and cartridge wall 136. These frictional characteristics, together with resistance to displacement of medical fluid 102 and buffering solution 124, are arranged to assure that pressure acting on slidable closure 142 first moves the slideable closure 142 within the cartridge 134, and thereafter moves the cartridge within the carpule 122 to expel the mixed solution. As a consequence, buffering solution 124 is discharged into and mixes with medical fluid 102 prior to the mixture being injected through needle 147 (FIG. 1).

Stop 146 has the following function. When slidable closure 142 is first contacted and urged towards needle 147, force from plunger 118 and a harpoon 150 causes slidable closure 142 to move within cartridge 134, without moving cartridge 134 within carpule 122 of syringe 100. When slidable closure 142 contacts stop 146, or alternatively, should slidable closure 142 pinch frangible barrier 141 against stop 146, continued force from plunger 118 will then move cartridge 134 along the inner surface of the carpule 122.

Therefore, a full stroke of plunger 118 first mixes buffering solution 124 with medical fluid 102, and subsequently injects the mixture. Alternatively stated, a first pressure on slideable closure 142 causes slideable closure 142 to advance within cartridge 134 towards frangible barrier 141, causing frangible barrier 141 to rupture. This allows first solution 124 to be expelled from first solution chamber 144 and into second solution chamber 145 and mix with second solution 102. Continued pressure on slideable closure 142 causes slideable closure 142 to eventually abut against stop 146, fully expelling first solution 124 into second solution chamber 145. A second pressure on slideable closure 142 abutting stop 146 causes cartridge 134 to advance within carpule body 126 towards injection end 130 of carpule 122, thereby expelling the mixture of first and second solutions 124, 102 from injection end 130 of carpule 122.

FIG. 1 shows an initial position of plunger 118 and carpule 122 within barrel 104 of syringe 100. In the initial position, syringe 100 is loaded with medical fluid 102 and buffering solution 124 (and optionally, the dye) in preparation to inject medical fluid 102 into the tissue of the patient. In the initial position of FIG. 1, position of cartridge 134 is aligned at the right in FIG. 1 with carpule 122.

Referring now to FIG. 2, the medical practioner (not shown) has started to apply manual pressure to thumb engaging surface 120, thereby displacing plunger 118 in a direction towards injection element 110. As seen in FIG. 2, slidable closure 142 responds to this motion by advancing within cartridge 134. Note that the cartridge 134 has not changed in position.

As indicated in FIG. 3, this advancement causes fluid pressure to burst frangible barrier 141, thereby enabling buffering solution (and optionally, dye) to mix with medical fluid 102. The dye enables the medical practitioner to observe introduction of buffering solution into medical fluid 102, thereby assuring that a buffered solution will be injected. In a similar vein, the medical practioner can observe lack of dye in medical fluid 102. This is important where for example medical fluid 102 is an anesthetic, since there is only a limited time window during which injection may be performed. The dye therefore can be used to indicate firstly, that the time window has not elapsed, and secondly, that buffering has been accomplished.

Turning to FIG. 4, continued advance of plunger 118 under the influence of manual pressure on thumb engaging surface 120 causes slideable closure 142 to eventually abut against stop 146, fully expelling first solution 124 into second solution chamber 145. A second pressure on slideable closure 142 abutting stop 146 causes cartridge 134 to advance within carpule body 126 towards injection end 130 of carpule 122, thereby expelling the mixture of first and second solutions 124, 102 from injection end 130 of carpule 122 and to be injected to the patient through needle 147. Fluid may be expelled from carpule 122 by rupturing a diaphragm (not shown) in a cap 156 (152) by pressure, or by forcing cap 156 against a piercing element (not shown) of needle 147.

Although description of syringe 100 refers to medical fluid 102 contained within carpule 122, the applicant contemplates that the novel principles may be applied where feasible to syringes which are initially charged by drawing medical fluids in by suction. An example is illustrated in FIG. 6, wherein syringe 100 has cartridge 134, but does not have carpule 122. Second solution chamber 145 is part of barrel 104 of syringe 100. Second solution 102 is contained in second solution chamber 145. First solution 124 is discharged into second solution 102 by pressure on plunger 118, just as in the embodiment of FIGS. 1-4. However, second solution 102 may be introduced into barrel 104 directly, prior to insertion of cartridge 134.

The present invention may be thought of as syringe 100 together with carpule 122, or alternatively, as only cartridge 134, or as only carpule 122 utilizing cartridge 134.

Figure 5:
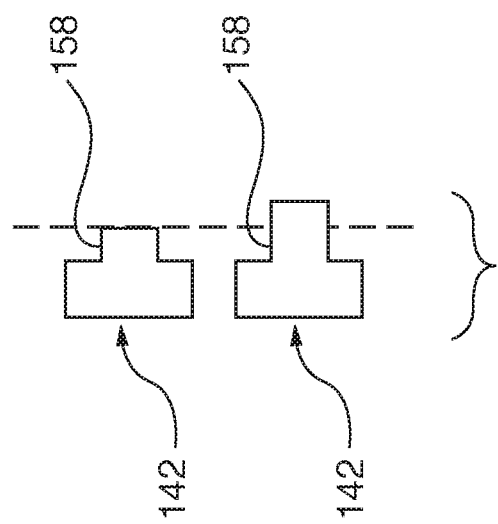
FIG. 5 is a side cross sectional detail view of variations of a component seen at the center of FIG. 1, according to at least one aspect of the invention.

The present invention may also be thought of as a cartridge kit for providing buffering solution 124 for carpule 122 for syringe 100. The cartridge kit may comprise a plurality of cartridges 134 generally similar to that described previously, but differing in the following way. Referring also to FIG. 5, cartridges 134 may include slidable closures 142 wherein slidable closure 142 of one carpule 122 or cartridge 134 further comprises a first tail projection 158 of one length (along longitudinal axis 108) projecting therefrom, and another slidable closure 142 of another carpule 122 or buffering cartridge 134 further comprises a tail projection 158 of another length projecting therefrom. The variation in dimensions of tail projections 158 enables different volumes of buffering solution 124 to be provided in otherwise identical cartridges 134. That portion of slidable closure 142 contacting cartridge wall 136 may remain identical, so that friction characteristics are constant, even across a large selection of cartridges 134. These cartridges 134, and thus carpules 122, will perform similarly even though different volumes of buffering solution 124 are mixed with medical fluid 102.

The carpule or cartridge kit may include the previously discussed dye.

The present invention will be understood to be applicable for a number of binary solutions which are mixed together at the last moment. While description herein is based on dental anesthesia, other possibilities are contemplated.

Although description of syringe 100 refers to medical fluid 102 contained within carpule 122, the applicant contemplates that the novel principles may be applied where feasible to syringes which are initially charged by drawing medical fluids in by suction.

While the disclosed concepts have been described in connection with what is considered the most practical and preferred implementation, it is to be understood that the disclosed concepts are not to be limited to the disclosed arrangements, but are intended to cover various arrangements which are included within the spirit and scope of the broadest possible interpretation of the appended claims so as to encompass all modifications and equivalent arrangements which are possible.

I claim:

1. A solution cartridge for storing and then dispensing a first solution into a second solution prior to injection of a mixed solution, the cartridge comprising:
   a body having a first end, an opposed second end, an exterior surface, and a central axis extending between the first end and the second end;
   a stop adjacent to the first end, the stop including a passageway extending entirely through the stop;
   a slidable closure within the cartridge;
   a frangible barrier configured to cover the passageway of the stop and rupture when the slidable closure is urged toward the first end;
   the slidable closure causing a solution chamber to exist within the cartridge between the frangible barrier and the slidable closure, wherein the slidable closure is dimensioned and configured to fit slidably and closely within the cartridge, to contact the cartridge, and to seal the solution chamber against fluid leakage when the slidable closure slides along the cartridge;
   a flexible external seal surrounding at least a portion of an external surface of the body of said cartridge; and
   one or more projections facing the frangible barrier such that when the frangible barrier is urged toward the first end, said one or more projections assist in rupturing said frangible barrier.

2. The cartridge of claim 1, wherein the slidable closure is arranged to slide in a direction parallel to the central axis.

3. The cartridge of claim 1, further comprising a buffering solution contained within the solution chamber.

4. The cartridge of claim 3, further comprising a dye of a predetermined color in the buffering solution.

5. The cartridge of claim 1 wherein the flexible external seal comprises a plurality of flexible polymeric rings.

* * * * *